US008764781B2

(12) United States Patent
Auchter et al.

(10) Patent No.: US 8,764,781 B2
(45) Date of Patent: *Jul. 1, 2014

(54) GUARDED SURGICAL KNIFE HANDLE

(75) Inventors: Gregory Allen Auchter, Reading, PA (US); Randal Lee Berardi, Ephrata, PA (US); David Robert Schiff, Highland Park, NJ (US); Seth McCue GaleWyrick, Asheville, NC (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,673

(22) Filed: Jul. 24, 2012

(65) Prior Publication Data

US 2012/0285023 A1 Nov. 15, 2012

Related U.S. Application Data

(63) Continuation of application No. 12/620,262, filed on Nov. 17, 2009, now Pat. No. 8,256,331.

(60) Provisional application No. 61/116,497, filed on Nov. 20, 2008.

(51) Int. Cl.
*A61B 17/32* (2006.01)
*B26B 3/00* (2006.01)

(52) U.S. Cl.
USPC .................. 606/167; 606/182; 30/2; 30/151

(58) Field of Classification Search
USPC ............... 30/2, 151, 162, 163, 335, 329, 339; 606/166, 167, 181, 182; 83/13
See application file for complete search history.

(56) References Cited

U.S. PATENT DOCUMENTS 1,735,271 A 11/1929 Groff
2,512,237 A 6/1950 Mravik
(Continued)

FOREIGN PATENT DOCUMENTS

DE 3722899 1/1989
EP 162170 11/1985
(Continued)

OTHER PUBLICATIONS

International Searching Authority, PCT International Preliminary Examination Report, PCT/GB01/01561, May 13, 2002, 2 pages.

(Continued)

*Primary Examiner* — Phong Nguyen
(74) *Attorney, Agent, or Firm* — Darien Reddick

(57) ABSTRACT

A guarded surgical knife handle includes a handle portion with a blade holder, a chamber within the handle portion, and a slot. The guarded surgical knife handle also includes a guard having an open distal end slidably mounted within the handle portion that can slide longitudinally between an unguarded position and a guarded position. The guard is sized to surround the blade in the guarded position. The guarded surgical knife handle also includes a latch that latches the guard when the guard is slid into the guarded position and a first button that disengages the latch. The guarded surgical knife handle includes a bias member that forces the guard in a proximal direction to an unguarded position when the latch is disengaged along with a second button extending through the slot used to slide the guard in a distal direction into the guarded position.

7 Claims, 3 Drawing Sheets

(56) References Cited

U.S. PATENT DOCUMENTS

| | | | |
|---|---|---|---|
| 3,748,736 | A | 7/1973 | Eisen |
| 3,793,726 | A | 2/1974 | Schrank |
| 3,905,101 | A | 9/1975 | Shepherd |
| 3,906,626 | A | 9/1975 | Riuli |
| 4,071,952 | A | 2/1978 | Meshulam et al. |
| 4,165,745 | A | 8/1979 | Heifetz |
| 4,414,974 | A | 11/1983 | Dotson et al. |
| 4,523,379 | A | 6/1985 | Osterhout et al. |
| 4,552,146 | A | 11/1985 | Jensen et al. |
| 4,576,164 | A | 3/1986 | Richeson |
| 4,635,914 | A | 1/1987 | Kabanek |
| 4,660,287 | A | 4/1987 | Decker |
| 4,674,500 | A | 6/1987 | DeSatnick |
| 4,733,662 | A | 3/1988 | DeSatnick et al. |
| 4,759,363 | A | 7/1988 | Jensen |
| 4,768,509 | A | 9/1988 | Grosvenor et al. |
| 4,790,312 | A | 12/1988 | Capuano, Sr. et al. |
| 4,896,983 | A | 1/1990 | Im et al. |
| 4,903,390 | A | 2/1990 | Vidal et al. |
| 5,026,386 | A | 6/1991 | Michelson |
| 5,059,210 | A | 10/1991 | Clark et al. |
| 5,092,852 | A | 3/1992 | Poling |
| 5,116,351 | A | 5/1992 | Frassetti |
| 5,201,748 | A | 4/1993 | Newman et al. |
| 5,207,696 | A | 5/1993 | Matwijcow |
| 5,234,436 | A | 8/1993 | Eaton et al. |
| 5,250,063 | A | 10/1993 | Abidin et al. |
| 5,250,064 | A | 10/1993 | Schneider |
| 5,254,128 | A | 10/1993 | Mesa |
| 5,275,606 | A | 1/1994 | Abidin et al. |
| 5,292,329 | A | 3/1994 | Werner |
| 5,299,357 | A | 4/1994 | Wonderley et al. |
| 5,309,641 | A | 5/1994 | Wonderley et al. |
| 5,330,492 | A | 7/1994 | Haugen |
| 5,330,494 | A | 7/1994 | van der Westhuizen et al. |
| 5,352,220 | A | 10/1994 | Abidin et al. |
| 5,391,177 | A | 2/1995 | Schwartz |
| 5,403,337 | A | 4/1995 | Platts |
| 5,411,512 | A | 5/1995 | Abidin et al. |
| 5,417,704 | A | 5/1995 | Wonderley |
| 5,475,925 | A | 12/1995 | Newman et al. |
| 5,496,340 | A | 3/1996 | Abidin et al. |
| 5,556,409 | A | 9/1996 | Haining |
| 5,569,281 | A | 10/1996 | Abidin et al. |
| 5,571,127 | A | 11/1996 | DeCampli |
| 5,571,128 | A | 11/1996 | Shapiro |
| 5,620,454 | A | 4/1997 | Pierce et al. |
| 5,683,407 | A | 11/1997 | Jolly et al. |
| 5,702,369 | A | 12/1997 | Mercereau |
| 5,741,289 | A | 4/1998 | Jolly et al. |
| 5,830,226 | A | 11/1998 | Webb et al. |
| 5,908,432 | A * | 6/1999 | Pan .................. 606/167 |
| 5,919,201 | A | 7/1999 | Carter et al. |
| 5,941,892 | A | 8/1999 | Cohn et al. |
| 6,022,364 | A | 2/2000 | Flumene et al. |
| 6,503,262 | B1 | 1/2003 | Edens |
| 6,569,175 | B1 | 5/2003 | Robinson |
| 6,623,499 | B1 | 9/2003 | Andreini et al. |
| 6,626,925 | B2 | 9/2003 | Newman et al. |
| D496,730 | S | 9/2004 | Morawski |
| 6,884,240 | B1 | 4/2005 | Dykes |
| 7,022,128 | B2 | 4/2006 | Morawski et al. |
| 7,087,067 | B2 | 8/2006 | Kehr et al. |
| 7,101,382 | B2 | 9/2006 | George et al. |
| 7,153,317 | B2 | 12/2006 | Kanodia et al. |
| 7,159,713 | B1 | 1/2007 | Austria |
| 7,175,643 | B2 * | 2/2007 | Shi ................... 606/181 |
| 7,387,637 | B2 | 6/2008 | Morawski et al. |
| 2002/0143352 | A1 | 10/2002 | Newman et al. |
| 2003/0074013 | A1 | 4/2003 | Schooler et al. |
| 2003/0225428 | A1 | 12/2003 | Saito et al. |
| 2004/0098004 | A1 | 5/2004 | George et al. |
| 2004/0111106 | A1 | 6/2004 | Iske et al. |
| 2004/0158269 | A1 | 8/2004 | Holman |
| 2004/0186496 | A1 | 9/2004 | Sandel et al. |
| 2004/0215174 | A1 | 10/2004 | Morawski et al. |
| 2004/0243161 | A1 | 12/2004 | Kanodia et al. |
| 2005/0015104 | A1 * | 1/2005 | Morawski et al. ......... 606/167 |
| 2005/0119680 | A1 | 6/2005 | Dykes |
| 2005/0267502 | A1 | 12/2005 | Hochman |
| 2006/0085019 | A1 | 4/2006 | Cote et al. |
| 2006/0100650 | A1 | 5/2006 | Kiehne |
| 2006/0241664 | A1 | 10/2006 | Lam |
| 2007/0255298 | A1 * | 11/2007 | Djordjevic et al. ......... 606/167 |
| 2008/0058843 | A1 | 3/2008 | Morawski et al. |
| 2008/0058844 | A1 | 3/2008 | Morawski et al. |
| 2008/0141539 | A1 * | 6/2008 | Co ..................... 30/162 |

FOREIGN PATENT DOCUMENTS

| | | |
|---|---|---|
| EP | 555196 | 8/1993 |
| EP | 583992 | 2/1994 |
| EP | 709064 | 5/1996 |
| EP | 727186 | 8/1996 |
| EP | 988832 | 3/2000 |
| WO | 92/15254 | 2/1992 |
| WO | 93/11916 | 6/1993 |
| WO | 93/21837 | 11/1993 |
| WO | 93/24064 | 12/1993 |
| WO | 95/15723 | 6/1995 |
| WO | 96/01080 | 1/1996 |
| WO | 97/37599 | 10/1997 |
| WO | 01/74257 | 10/2001 |
| WO | 03/099145 | 12/2003 |
| WO | 2004/026151 | 4/2004 |
| WO | 2005/089202 | 9/2005 |

OTHER PUBLICATIONS

International Searching Authority, PCT International Preliminary Examination Report, PCT/AU03/001187, Jan. 17, 2005, 8 pages.

* cited by examiner

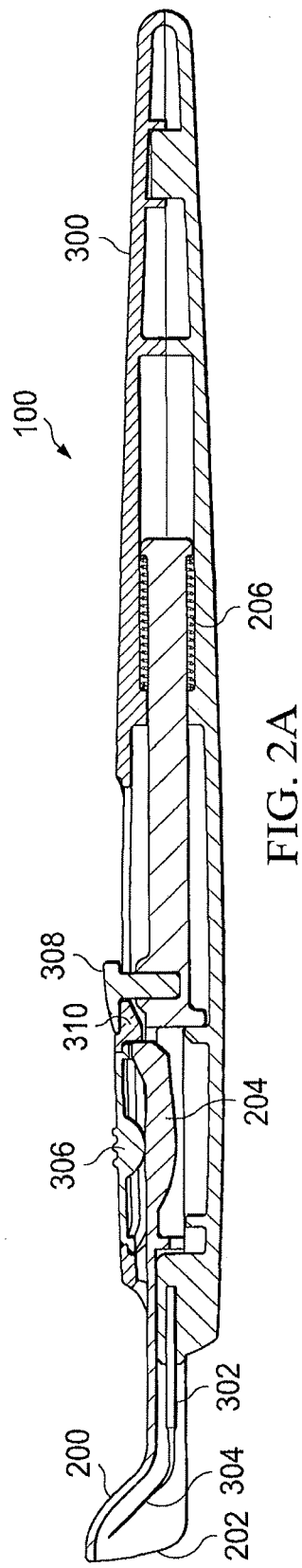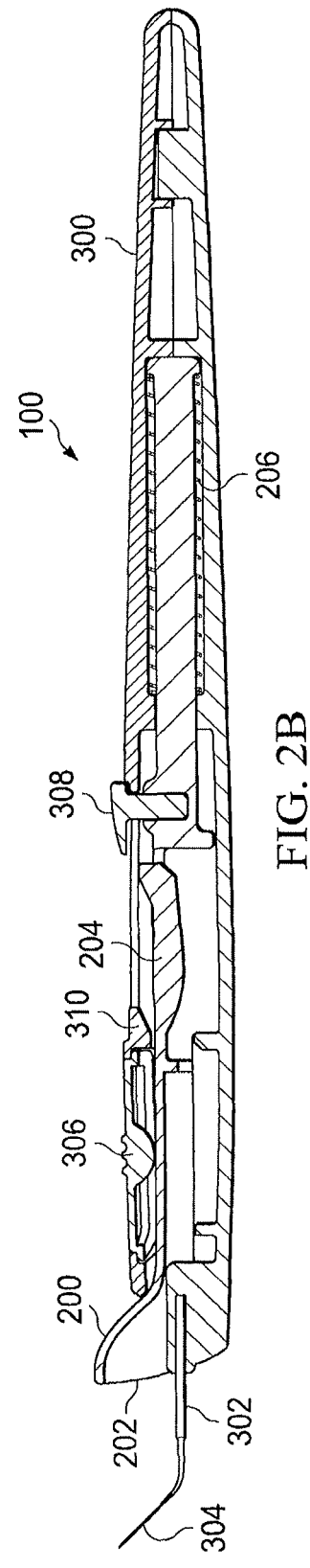

FIGURE 3 (400)

START

Provide guarded surgical knife handle latched in guarded position (402)

Disengage latch using first button (404)

Slide guard into guarded position using second button (406)

END ed position.

GUARDED SURGICAL KNIFE HANDLE

CROSS REFERENCE TO RELATED APPLICATIONS

This application is a continuation application of application Ser. No. 12/620,262, filed Nov. 17, 2009, now U.S. Pat. No. 8,256,331 which claims the benefit of U.S. Provisional Application No. 61/116,497, filed on Nov. 20, 2008, the contents of both being incorporated herein by reference.

SUMMARY

In particular embodiments of the present invention, a guarded surgical knife handle includes a handle portion with a blade holder, a chamber within the handle portion, and a slot. The guarded surgical knife handle also includes a guard having an open distal end slidably mounted within the handle portion that can slide longitudinally between an unguarded position and a guarded position. The guard is sized to surround the blade in the guarded position. The guarded surgical knife handle also includes a latch that latches the guard when the guard is slid into the guarded position and a first button that disengages the latch. The guarded surgical knife handle includes a bias member that forces the guard in a proximal direction to an unguarded position when the latch is disengaged along with a second button extending through the slot used to slide the guard in a distal direction into the guarded position.

In other embodiments of the present invention, a method for unguarding and guarding a surgical knife includes providing a guarded surgical knife with a handle portion including a blade and a slot. The guarded surgical knife also includes a guard having an open distal end slidably mounted within the handle portion. The guard is latched by a latch in a guarded position. The method also includes disengaging the latch using a button to allow a bias member to force the guard in a proximal direction. The method further includes sliding the guard to the guarded position to re-engage the latch.

BRIEF DESCRIPTION OF THE DRAWINGS

FIGS. 2A and 2B illustrate the guarded surgical knife handle of FIG. 1 in a guarded and unguarded position, respectively; and FIG. 3 is a flow chart showing an example method of unguarding and guarding a surgical knife according to a particular embodiment of the present invention.

DETAILED DESCRIPTION

Figure 1:
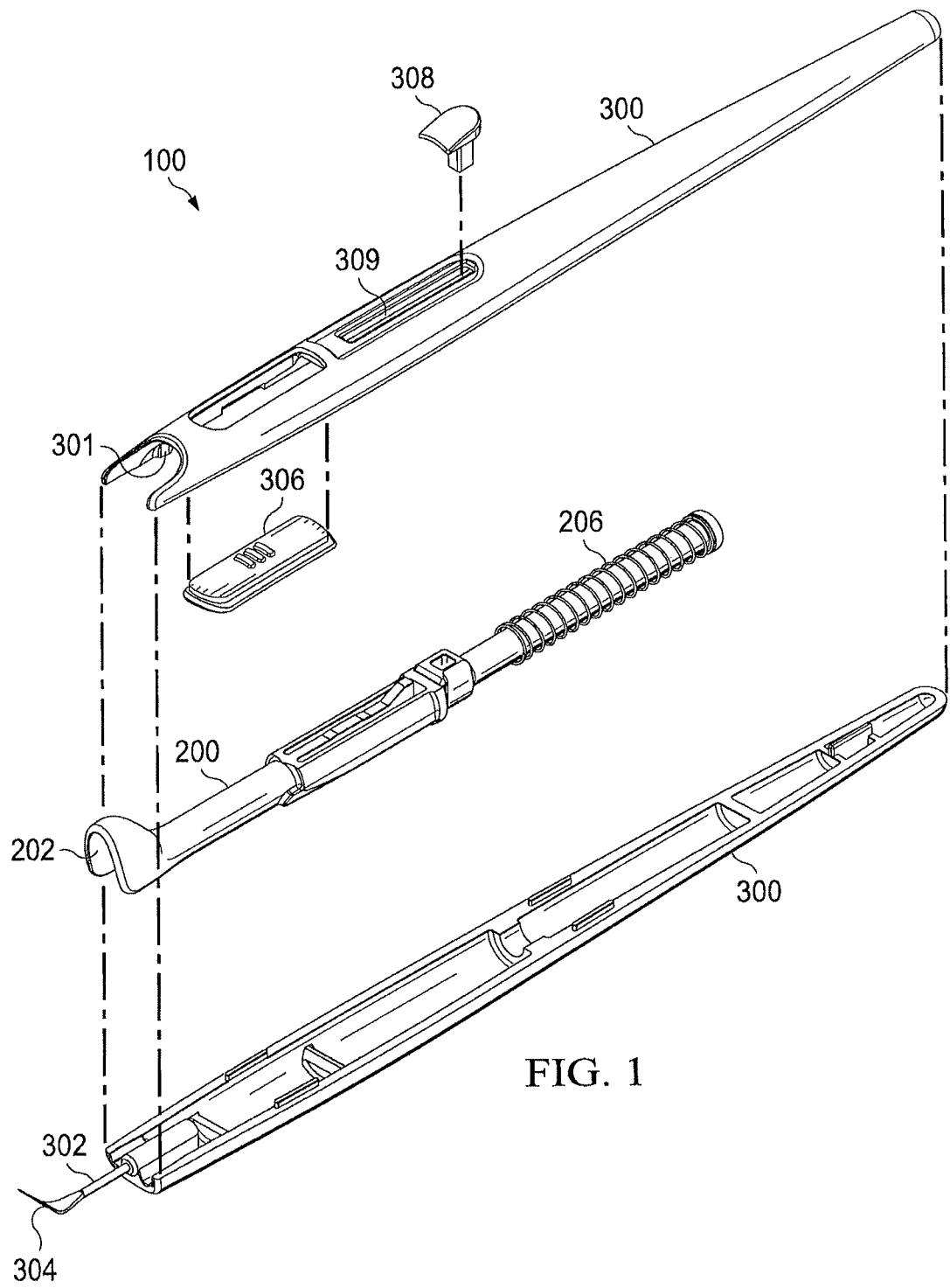
FIG. 1 is a disassembled view of a guarded surgical knife handle according to a particular embodiment of the present invention.

For purposes of this description, the following conventions are employed in naming various locations of the guarded surgical knife handle. "Longitudinal" describes a direction generally along an axis between one end of the guarded surgical knife that holds a blade in proximity to a patient and the opposite end near the surgeon. "Proximal" describes a location relatively closer to the surgeon than the patient in the longitudinal direction; conversely, "distal" refers to a location that is closer to the patient. "Upper," "lower," "top," and "bottom" describe locations in terms of the orientation of the guarded surgical knife handle as it is held by a surgeon to perform incisions on a patient. "Vertical" describes a direction generally along an axis between the top and bottom of the guarded surgical knife handle, while "height" measures a distance in a vertical direction. "Lateral" describes a direction generally along an axis perpendicular to the longitudinal and vertical directions, corresponding generally to left and right directions from the surgeon's perspective.

FIG. 1 illustrates a disassembled view of various components of a guarded surgical knife handle 100 according to a particular embodiment of the present invention, FIG. 2A is a cross-section of the assembled guarded surgical knife 100 in a guarded position, and FIG. 2B is a cross-section of the guarded surgical knife 100 in an unguarded position. The guarded surgical knife handle 100 includes a guard 200 with an open distal end 202 slidably mounted in a chamber formed within a handle portion 300 (shown in two pieces in FIG. 1). The handle portion 300 includes a blade holder 302 adapted to hold a blade 304.

The blade 304 may be any sort of blade suitable for surgical incisions and may have a straight or curved edge. In various embodiments of the present invention, the blade 304 may be straight or may be inclined at a particular height and angle (as depicted in FIG. 1), and the guarded surgical knife handle 100 may have colored portions according to a predetermined color code to indicate the type of blade for the guarded surgical knife handle 100. The guard 200 is sized appropriately for the particular type of blade 304, which may be done, for example, by increasing the height of the guard 200 at the open distal end 202. A notch 301 sized to receive the portion of the guard 200 having a greater height may be provided in the handle portion 300. The relative height of the blade holder 302 above a bottom of the lower handle portion 300 may also be selected to facilitate use of the blade 304 during surgery and to easily fit the guard portion 202 around the blade 304. For example, a blade holder 302 used to hold a straight blade might hold the point of blade at a height approximately in the middle of guarded surgical knife, while a blade holder 302 for a blade with a larger height might be placed at the bottom of the lower handle portion 300.

The guard 200 may also include additional safety features to further reduce the likelihood of inadvertent contact with the blade 304. For example, if the guard 200 has a height and/or width sufficiently large to admit a finger at the open distal end 202, the guard 200 may include narrowing features such as internal ribs (not shown) to prevent the finger from entering the guard 200. The guarded surgical knife handle 100 may also include features to prevent the guard 200 from being displaced so as to contact the blade 304. The guard 200 may also be advantageously configured to allow the surgeon to more easily visualize the blade 304. For example, the guard 200 may be formed partially or entirely from a transparent material, so that the surgeon can see the blade in both the guarded and unguarded positions.

The guarded surgical knife handle 100 includes a latch 204 and a bias member 206. The latch 204 holds the guard 200 in a guarded position, while the bias member 206 forces the guard 200 in a proximal direction when the latch 204 is disengaged. In the depicted embodiment, the bias member 206 is a coil spring, but other suitable mechanical arrangements for forcing the guard 200 in the proximal direction could also be used. In the guarded position, the latch 204 is held against a detent 310 by the force of the bias member 206. A button 306 is depressed to push the latch 204 down below the detent 310, thus disengaging the latch 204 and allowing the guard 200 to slide in the proximal direction due to the force exerted by the bias member 206.

To return the guard 200 to the guarded position, a second button 308 is provided that extends through a slot 309 in the handle portion 300. The second button 308 is used to slide the guard 200 back into the guarded position. As the guard 200 slides forward, the latch 204 is pushed down by the detent 310. Once the latch 204 passes the detent 310, the latch 204 pops up to rest behind the detent 310, thus re-engaging the latch 204 and latching the guard 200 in the guarded position. Although a particular embodiment of the latch mechanism has been described, other alternative embodiments will be readily apparent to one skilled in the art. For example, the button 306 could be a trigger beneath the guarded surgical knife handle 100 that lowers a detent latching the guard 200 in place. In general, any suitable mechanism for holding the guard 200 in place against the force exerted by the bias member 206 may be used for the latch 204.

The buttons 306 and 308 may include textured surfaces to facilitate gripping the guarded surgical knife handle 100 and to provide a tactile indication of the location of the buttons 306 and 308. Additionally, a bottom grip feature (not shown) may be extend from the bottom of the handle portion 300 to allow a secure finger hold and to permit the surgeon to hold the guarded surgical knife handle 100 more securely while the button 308 is being slid. The bottom grip feature may advantageously include a flattened bottom surface that prevents the guarded surgical knife handle 100 from rolling when it is set down on a level, flat surface. A textured grip surface may also be placed adjacent to the bottom grip feature to make the surgeon's grip on the guarded surgical knife handle even more secure.

FIG. 3 is a flow chart 400 illustrating an example method of unguarding and guarding a guarded surgical knife handle 100 according to a particular embodiment of the present invention. At step 402, a guarded surgical knife handle 100 is provided with the latch 204 engaged. At step 404, the latch 204 is disengaged by pressing the button 306, thus allowing the bias member 206 to force the guard 200 proximally into an unguarded position. At step 406, the guard 200 is slid using the button 308 back into the guarded position, thus re-engaging the latch 204.

The present invention has been described by reference to certain preferred embodiments; however, it should be understood that it may be embodied in other specific forms or variations thereof without departing from its essential characteristics. The embodiments described above are therefore considered to be illustrative in all respects and not restrictive, the scope of the invention being indicated by the appended claims.

The invention claimed is:

1. A guarded surgical knife handle, comprising:
    a handle portion comprising a blade holder adapted to hold a blade, a chamber within the handle portion, a detent, and a slot;
    a guard having an open distal end slidably mounted within the handle portion and operable to slide longitudinally between an unguarded position and a guarded position, wherein the guard is sized to surround the blade in the guarded position;
    a cantilevered latch formed on the guard, the latch operable to engage the detent to latch the guard when the guard is slid into the guarded position;
    a first button operable to disengage the latch;
    a bias member configured to force the guard in a proximal direction to an unguarded position when the latch is disengaged; and
    a second button extending through the slot and operable to slide the guard in a distal direction into the guarded position.

2. The guarded surgical knife handle of claim 1, wherein the guard comprises a transparent material.

3. The guarded surgical knife handle of claim 1, wherein the bias member comprises a coil spring.

4. The guarded surgical knife handle of claim 1, wherein the distal end of the guard has a relatively greater height such that the distal end is sized to fit around the blade.

5. The guarded surgical knife handle of claim 4, wherein the handle comprises a notch, and the notch is sized to receive the portion of the guard with the relatively greater height.

6. The guarded surgical knife handle of claim 1, wherein the blade holder is located at a bottom surface of the handle portion.

7. The guarded surgical knife handle of claim 1, wherein the first button comprises a textured top surface.

* * * * *